US007129080B2

(12) United States Patent
Antloga et al.

(10) Patent No.: US 7,129,080 B2
(45) Date of Patent: Oct. 31, 2006

(54) VITRO MODEL OF PRIOCIDAL ACTIVITY

(75) Inventors: Kathleen M. Antloga, Chardon, OH (US); Gerald E. McDonnell, Chardon, OH (US)

(73) Assignee: Steris Inc., Temecula, CA (US)

( * ) Notice: Subject to any disclaimer, the term of this patent is extended or adjusted under 35 U.S.C. 154(b) by 412 days.

(21) Appl. No.: 10/264,606

(22) Filed: Oct. 4, 2002

(65) Prior Publication Data

US 2003/0148385 A1 Aug. 7, 2003

Related U.S. Application Data

(60) Provisional application No. 60/327,460, filed on Oct. 5, 2001.

(51) Int. Cl.
*A01N 25/00* (2006.01)
*A01L 2/00* (2006.01)
*A61L 2/16* (2006.01)
*A61L 101/00* (2006.01)

(52) U.S. Cl. ........................... 435/262; 422/1; 422/28; 422/30

(58) Field of Classification Search ................ 435/272, 435/267, 262; 422/1, 28, 30
See application file for complete search history.

(56) References Cited

U.S. PATENT DOCUMENTS

| | | | | |
|---|---|---|---|---|
| 3,941,696 | A | 3/1976 | Melnick et al. | |
| 4,169,123 | A | 9/1979 | Moore et al. | |
| 4,473,550 | A | 9/1984 | Rosenbaum et al. | |
| 4,973,449 | A | 11/1990 | Kolstad et al. | |
| 5,007,232 | A | 4/1991 | Caudill | |
| 5,116,575 | A | 5/1992 | Badertscher et al. | |
| 5,145,642 | A | 9/1992 | Feathers, III et al. | |
| 5,173,259 | A | 12/1992 | Bordini | |
| 5,178,841 | A | 1/1993 | Vokins et al. | |
| 5,258,162 | A | 11/1993 | Andersson et al. | |
| 5,260,021 | A | 11/1993 | Zeleznick | |
| 5,567,444 | A | 10/1996 | Hei et al. | |
| 5,600,142 | A | 2/1997 | Van Den Berg et al. | |
| 5,634,880 | A | 6/1997 | Feldman et al. | |
| 5,674,450 | A | 10/1997 | Lin et al. | |
| 5,733,503 | A | 3/1998 | Kowatsch et al. | |
| 5,756,678 | A | 5/1998 | Shenoy et al. | |
| 5,779,973 | A | 7/1998 | Edwards et al. | |
| 5,788,925 | A | 8/1998 | Pai et al. | |
| 5,792,435 | A | 8/1998 | Mueller et al. | |
| 5,837,193 | A | 11/1998 | Childers et al. | |
| 5,848,515 | A | 12/1998 | Catelli et al. | |
| 5,872,359 | A | 2/1999 | Stewart et al. | |
| 5,876,664 | A | 3/1999 | Childers et al. | |
| 6,010,994 | A | 1/2000 | Choy et al. | |
| 6,094,523 | A | 7/2000 | Zelina et al. | |
| 6,162,055 | A | 12/2000 | Montgomery et al. | |
| 6,322,802 | B1 | 11/2001 | Prusiner et al. | 424/405 |
| 6,387,858 | B1 | 5/2002 | Shah et al. | |
| 6,395,506 | B1 * | 5/2002 | Pitner et al. | 435/32 |
| 6,448,062 | B1 | 9/2002 | Huth et al. | |
| 6,488,965 | B1 | 12/2002 | Karageozian | |
| 6,503,881 | B1 * | 1/2003 | Krieger et al. | 514/2 |
| 6,660,289 | B1 | 12/2003 | Wilmotte et al. | |
| 6,696,074 | B1 | 2/2004 | Dai et al. | |
| 6,767,712 | B1 | 7/2004 | Prusiner et al. | 435/7.23 |
| 6,875,399 | B1 | 4/2005 | McVey | |
| 2003/0086820 | A1 | 5/2003 | McDonnell et al. | |

FOREIGN PATENT DOCUMENTS

| | | |
|---|---|---|
| EP | 774 263 A1 | 5/1997 |
| FR | 2759589 | 8/1998 |
| FR | 2814177 | 3/2002 |
| GB | 2391785 A | 2/2004 |
| WO | WO 94/22305 | 10/1994 |
| WO | WO 98/15297 | 4/1998 |
| WO | WO/00 71575 | 11/2000 |
| WO | WO/01 00235 | 1/2001 |
| WO | WO 01/54736 A2 | 8/2001 |

OTHER PUBLICATIONS

Aguzzi et al. "Recent advances in prion biology" Current Opinions in Neurology (2004) 17: 337-342.*

Denys et al. "Microbiocial efficacy of the STERIS EcoCycle 10 biohazardous waste destruction, decontamination and disposal system" Abstracts of the General Meeting of the American Society for Microbiology (1995) vol. 95, No. 0, pp. 445, abstract only.*

Dyas et al. "Studies of novel agent possessing resistance to moist heat and disinfectants" parallels with Creutzfeldt-Jakob agent J. Hosp. Infection (1990) 15(3): 265-272□□.*

Sklaviadis et al. "Physical properties of the Creutzfeldt-Jakob disease agent" J. Virol. 63(3): 1212-1222.*

(Continued)

*Primary Examiner*—Jean C. Witz
*Assistant Examiner*—Susan Hanley
(74) *Attorney, Agent, or Firm*—Fay, Sharpe, Fagan, Minnich & McKee, LLP

(57) ABSTRACT

A proteinaceous material has been found to show similar activity and treatment response to that of disease causing prions, such as CJD. A prion model which incorporates the proteinaceous material has a variety of applications. The model has an ability to be cultured either in vivo or in vitro, allowing rapid screening of potential drugs for treating animals or humans, or methods of treating food products or items which may come into contact with prions, such as medical or dental devices. Several treatment methods and materials have been developed using the model.

14 Claims, 3 Drawing Sheets

OTHER PUBLICATIONS

Ohlson, CWRU Magazine, Summer 2001, vol. 13, No. 4, pp. 22-24; "On the Trail of A Dread Disease".

Burdon, J. Med. Microbiol, vol. 29 (1989), pp. 145-157; "A Novel Replicating Agent Isolated From the Human Intestinal Tract Having Characteristics Shared With Creutzfeldt-Jakob and Related Agents".

Burdon, et al. J. Med. Microbiol, vol. 45 (1996), pp. 10-15; "Replication of IFDO On a Chemically Defined Medium".

Burdon, The Lancet, vol. 353, Apr. 10, 1999; p. 1271; "Does Variant Creutzfeldt-Jakob Disease Have an Achilles Heel"?.

ASAIO Journal 2000, "Prion Disease and Medical Devices," by Antloga, et al. Nov./Dec.

Burdon, et al., "Replication of IFDO on a Chemically Defined Medium", Journ. Of Medical Microbiology, V. 45, N. 1, 1996, pp. 10-15 XP-002249888—(Abstract).

GMT Global Medical Technologies, Ltd. Product Information "Ecocycle 10" http://www.globalmedicaltechnologies.com/view_prd.php?code=bw0002 Sep. 15, 2005.

MSDS data sheet for the STERIS 20® Sterilant Concentrate.

Rutala, et al., "Creutzfeldt-Jakob Disease: Recommendations for Disinfection and Sterilization", Clinical Infectious Diseases, V. 32, N. 9, May 2001, pp. 1348-1356 XP008012867.

Darbord, "Inactivation of Prions in Daily Medical Practice", Biomedicine & Pharmacotherapy, V. 53, 1999, pp. 34-38 XP002228686.

Samson, "Stérilisation du materiel de dermato-chirurgie au cabinet du dermatologue" Nouvelle Dermatologiques, V. 19, N. 1, 2000 pp. 57-60 XP008012868.

Baron, et al., "Prions" in Disinfection, Sterilization and Preservation (Ed. S.S. Block); 5th Ed. pp. 659-674, Lippincott, Williams & Williams, NY.

Disinfection, Sterilization and Preservation (Ed. S.S. Block); 4th Ed. pp. 436-439 (Dec. 2000).

Yon, "Protein Folding: A Persepective for Biology, Medicine & Biotechnology", Brazilian Journal of Medical & Biological Research (2001) 34: 419-435 ISSN 0100-879X.

Ernst, et al., "Comparative Analysis of Scrapie Agent Inactivation Methods", Journal of Virological Methods, 41 (1993) 193-202 XP-002316603.

Brown, et al., "Effect of Chemicals, Heat and Histopathologic Processing on High-Infectivity Hamster-Adapted Scrapie Virus", Journ. of Infectious Diseases, vol. 145, No. 5, May 1982 pp. 683-687.

\* cited by examiner

VITRO MODEL OF PRIOCIDAL ACTIVITY

This Application claims the Priority of U.S. Provisional Application Ser. No. 60/327,460, filed Oct. 5, 2001.

BACKGROUND OF THE INVENTION

The present invention relates to the field of infectious diseases. It finds particular application as a method of evaluating the response of Prions (Proteinaceous Infectious Agents) to various treatments, and will be described with particular reference thereto. It should be appreciated, however, that the invention is also applicable to other studies of prion activity.

The term "Prion" is used to describe proteinaceous-infectious agents that cause relatively similar brain diseases in humans and/or in animals, which are invariably fatal. These diseases are generally referred to as transmissible spongiform encephalopathies (TSEs). TSEs include Creutzfeldt-Jakob disease (CJD) and variant CJD (vCJD) in humans, Bovine Spongiform Encephalopathy (BSE) in cattle, also know as "Mad Cow Disease," Scrapie in sheep, and Wasting Disease in elk. All of these diseases attack the neurological organs of the animal or animals which are susceptible to the particular disease. They are characterized by initially long incubation times followed by a short period of neurological symptoms, including dementia and loss of coordination, and eventually death.

The infectious agent responsible for these diseases is thought to be a simple protein, with no associated nucleic acids. The pathogenic mechanism for such prion diseases is proposed to involve an initially normal host encoded protein. The protein undergoes a conformational change to an abnormal form (a prion), which has the ability of self-propagation. The exact cause of this change is, at present, unknown. The abnormal form of the protein is not broken down effectively in the body and its accumulation in certain tissues (in particular neural tissue) eventually causes tissue damage, such as cell death. Once significant neural tissue damage has occurred, the clinical signs are observed.

Prion diseases may thus be classified as protein aggregation diseases, which also include several other fatal diseases, such as Alzheimer's disease and amyloidosis. In the case of CJD, the most prevalent prion disease in humans (occurring in roughly 1:1,000,000 of the population), about 85% of cases are thought to arise sporadically, about 10% are thought to be inherited, and about 5% arise iatrogenically.

There are currently no known effective treatments for prion diseases in animals or humans, and death thus follows the onset of neurological symptoms. Progress in the identification of target treatment drugs has been slow, due to the inability to perform testing in vitro. To date, no methods for culturing prions in media in the laboratory have been developed. In vivo studies involve inoculating a test animal with prions and examining the animal's response to a proposed treatment regime. Because progress of the disease is slow, these in vivo studies are inevitably lengthy and are thus not readily amenable to the screening of large numbers of potential drugs. In vivo mouse or hamster models have been engineered to be more susceptible to prions and are generally used for evaluations. In addition, because these diseases tend to be animal specific, it is not known whether tests done on animals can be readily applied to humans.

Some research groups have suggested using a yeast prion model for drug evaluation and there has been some reports of an in vitro model to study prion folding. However, there have been no studies which have established correlations between the behavior of these proposed models and prion activity.

In the early 1980's, a novel replicating agent was isolated from the human intestinal tract. (Burdon, *J. Med. Micro.*, 29: 145–157 (1989)). This agent was isolated from the ileostomy fluid (filtered through a $0.2\mu$ filter) of two patients with Crohn's disease, and could be cultured in vitro. It was given the name Ileal Fluid Dependent Organism (IFDO), although it has been subsequently found to survive in other media, such as in the presence of pancreatin. Discrete brown colonies were observed on a specific, select growth media. On examination of this agent, it did not appear to be viral, bacterial, or fungal in nature, but did appear to grow logarithmically and have unusual resistance to a variety of antibiotics, and physical and chemical agents. The agent was also found to have a high resistance to moist heat. This agent has not previously been directly linked to prions or used in prion research.

Although prion diseases have not generally been considered to be highly contagious, they can be transmitted within a species and, under certain conditions, from one species to another. It has recently been shown that prion diseases may be transmitted via high risk tissues, including the brain, spinal cord, and eye. Iatrogenic transmission has also been reported, including transmission via dura mater grafting, corneal transplants, pericardial homografts, human gonadotropin, and human growth hormone contamination. Transmission via medical devices has also been reported, including through reuse of neurosurgical instruments, depth electrodes, and other devices used during surgeries in close proximity to the central nervous system.

There is currently much speculation about the efficacy of conventional decontamination and sterilization methods for destruction of prions. Prions are notoriously very hardy and demonstrate resistance to routine methods of decontamination and sterilization. Some recommended methods include incineration, prolonged steam autoclaving, sodium hydroxide and sodium hypochlorite treatments at high concentrations (e.g., 1M NaOH or $NaHClO_3$ at 2% available Cl for 1 hr.). These aggressive treatments are often incompatible with medical devices, particularly flexible endoscopes and other devices with plastic, brass, or aluminum parts. Many devices are damaged by exposure to high temperatures. Chemical treatments, such as strong alkali, are damaging to medical device materials or surfaces in general. Glutaraldehyde, formaldehyde, hydrogen peroxide, most phenolics, alcohols, and processes such as dry heat, boiling, freezing, UV, ionizing, and microwave radiation have generally been reported to be ineffective. There is a clear need for products and processes that are effective against prions yet compatible with surfaces.

One less aggressive treatment which has been investigated and shown to be effective against prions is a peracetic acid formulation formulated by STERIS Corporation, Mentor, Ohio, under the tradename STERIS 20™. The formulation contains peracetic acid in a blend of buffers, anticorrosives, surfactants, and chelators, prepared in a use dilution for sterile processing at above room temperature.

However, there is currently no ready means of evaluating anti-prion ("priocidal") treatments. Culturing prion-treated devices after proposed priocidal treatments involves inoculating animals with washings from the devices and observing the development of the disease if the priocidal treatment is ineffective. This is a lengthy process and prone to errors, since the numbers of prions remaining on the devices may be relatively small. Additionally, there is a risk that prions which are not destroyed by the priocidal treatment may pose hazards to workers.

There are thus increased concerns among medical personnel regarding the proper care of patients identified as having prion diseases. There are also concerns that the diseases may be transmitted, through reuse of instruments and the like, due to a failure to detect the disease state prior to death of the infected patient. Additionally, the risks associated with high, medium, and low risk tissues have not yet been established. For example, tonsillectomy and dental procedures have been considered to be low risk procedures for potential prion infection. However, recent evidence suggests the risks may higher, due to the finding that prion infected tissues are being found outside the brain. It has also been suggested that there may be a link between prion-related diseases and similar disease states, such as Parkinson's and Alzheimer's diseases.

The present invention provides a new and improved method for evaluation of priocidal activity, which overcomes the above-referenced problems, and others.

SUMMARY OF THE INVENTION

In accordance with one aspect of the present invention, a method for evaluating potential treatments for activity against prions or prion-related diseases is provided. The method includes subjecting a prion model to the treatment, the prion model being one which has been shown to exhibit a response similar to that of prions to a treatment designed to attack prions and evaluating the effect of the treatment on the prion model as an indicator of the effect of the treatment on the prion or prion-related disease.

In accordance with another aspect of the present invention, a method of treating an item which may be contaminated with prions is provided. The method includes treating the item with a composition which includes at least one of nisin, manganese, and silver nitrate to reduce the level of viable prions on the item.

In accordance with another aspect of the present invention, a method of screening proposed drugs for activity against prion related diseases or proposed treatment processes or chemicals for priocidal activity is provided. The method includes exposing a prion model to the proposed drug, chemical, or process and culturing any remaining prion model in vitro, the prion model having been shown to exhibit similar responses to prions to a drug, chemical, or process.

In accordance with another aspect of the present invention, a method of treating a subject having a prion related disease is provided. The method includes treating a sample contaminated with an IFDO with a proposed treatment agent, the IFDO having been shown to respond to other treatment agents in a similar manner to the prion. If the treatment agent is effective at attacking the IFDO, treating the subject with the treatment agent in an effective amount.

One advantage of the present invention is that proposed prion disease treatments, pharmaceuticals, and priocidal agents can be screened in vitro, without the need for extensive in vivo study.

Another advantage of the present invention is that proposed prion disease treatments and priocidal agents can be evaluated rapidly.

Another advantage of the present invention is that prion-contaminated instruments, hard surfaces, and food products are rendered safer for use.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

Figure 1:
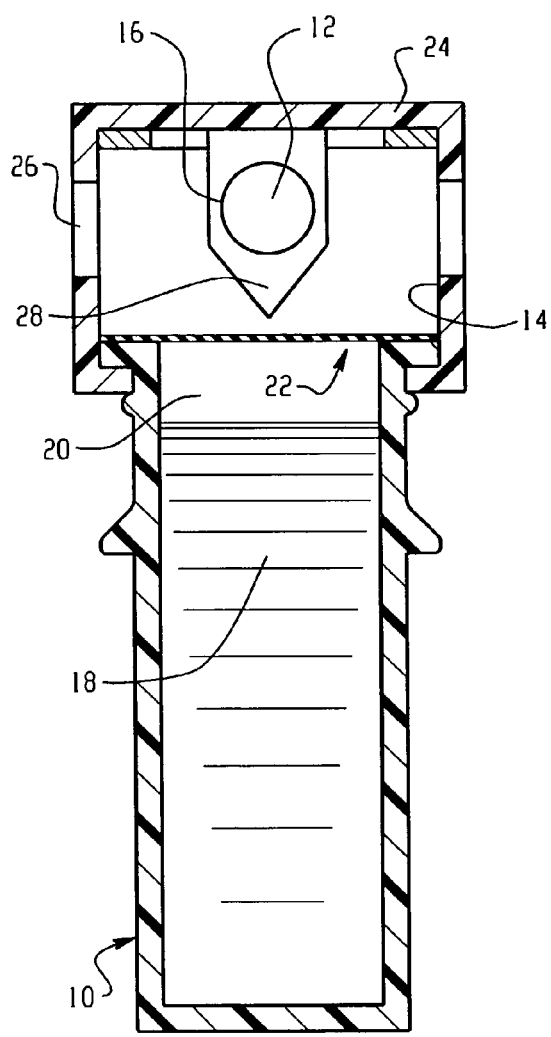
FIG. 1 is a schematic side view of a biological indicator containing a prion model according to the present invention.
Figure 2:
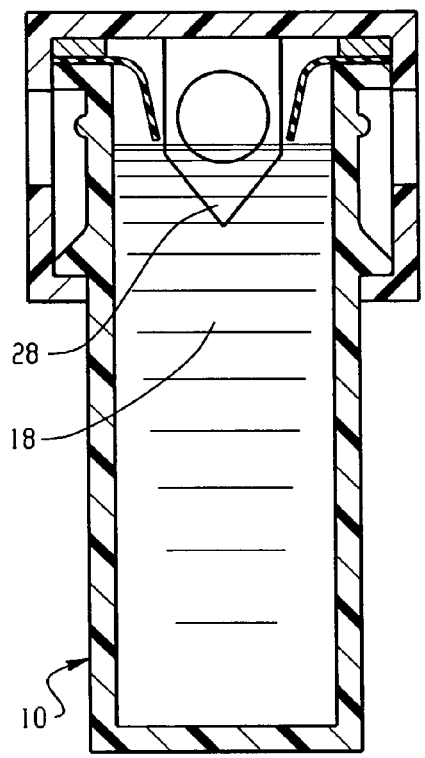
FIG. 2 is a schematic side view of the biological indicator of FIG. 1 after closing a cap to seal the indicator and mix the prion model with growth media.
Figure 3:
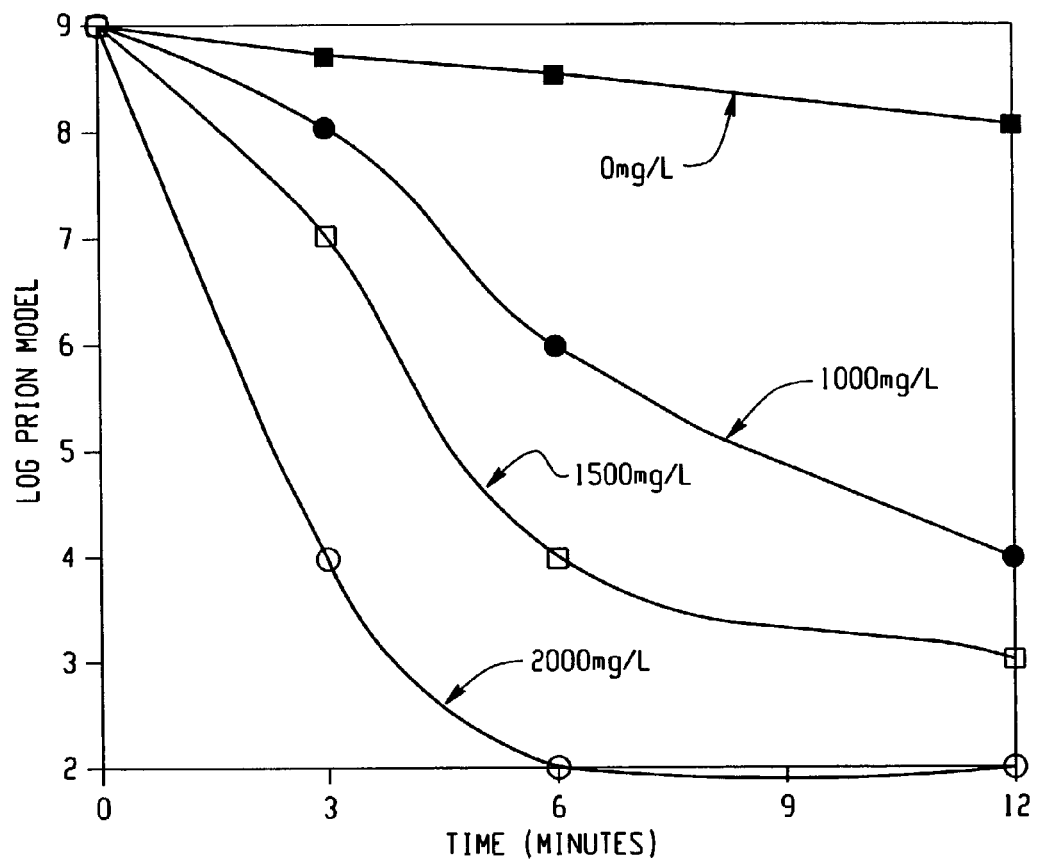
FIG. 3 is a plot of prion model count against time for peracetic acid treatment processes at different initial concentration levels of peracetic acid;

FIG. 4 is a plot showing the total number of red blood cells over time for a first control sample (water-RBC), a second control sample (pancreatin-Panc) and a sample of the prion model (labeled IFD0);

FIG. 5 is a plot of percent red blood cells having a normal structure (i.e., free of abnormal structure or aberrations) over time for a first control sample (water-RBC), a second control sample (pancreatin-Panc) and a sample of the prion model (labeled IFD0).

DETAILED DESCRIPTION OF THE PREFERRED EMBODIMENTS

An unusual proteinaceous entity which will be referred to herein as the "test protein" or "prion model" has been found to correlate with prion activity and is thus useful as simulated prion model. The prion model has been developed as an indicator for prion inhibition/inactivation and has shown correlation to prion inactivation in vitro and in vivo.

The preferred test protein was originally isolated by D. W. Burdon, Department of Microbiology, Queen Elizabeth Hospital, Birmingham, England. It was originally extracted from ileal fluid from patients suffering from Crohn's disease and is proteinaceous in nature. It appears to have associated iron and may have an RNA component. Microscopic examination at 100× shows the prion model to comprise pleomorphic particles of no uniform size or shape. We have subsequently shown this agent to be present in blood and serum samples.

It is contemplated, however, that other similar proteins, which show the same or similar resistance to destructive treatments as the present test model, may alternatively be used as the prion model.

The test protein is readily cultured in an artificial medium, such as agar-based media or liquid media. It can be used in the medium or suspended in water or other fluid. The protein appears to grow effectively when lysed red blood cells are present, thus it is preferable that the media contain red blood cells from humans or other animals, or extracts therefrom, such as hemoglobin. Since the prion model has been found in a sizeable proportion of blood samples, it is preferable for the blood to be screened prior to use in the growth medium to avoid any competing reactions in vitro and contamination of samples later to be cultured in vivo.

Very few actives have to date been shown to be effective at inhibiting the growth of the prion model in culture media. Of those found to have an effect, a number of these have previously been shown to have some activity against prions including vCJD, showing the correlation of the model with actual prion activity. These effective actives include sodium hydroxide (about 1M NaOH) and a phenol-based formulation sold under the tradename LpH™ by STERIS Corporation, Mentor, Ohio. A peracetic-acid based formulation, STERIS 20™, has previously been found to have activity against prions and has now been found to have activity against the prion model. Other actives with measurable activity, which have now been identified using the prion model, include nisin, neomycin sulphate, silver nitrate, and manganese.
Figure 4:
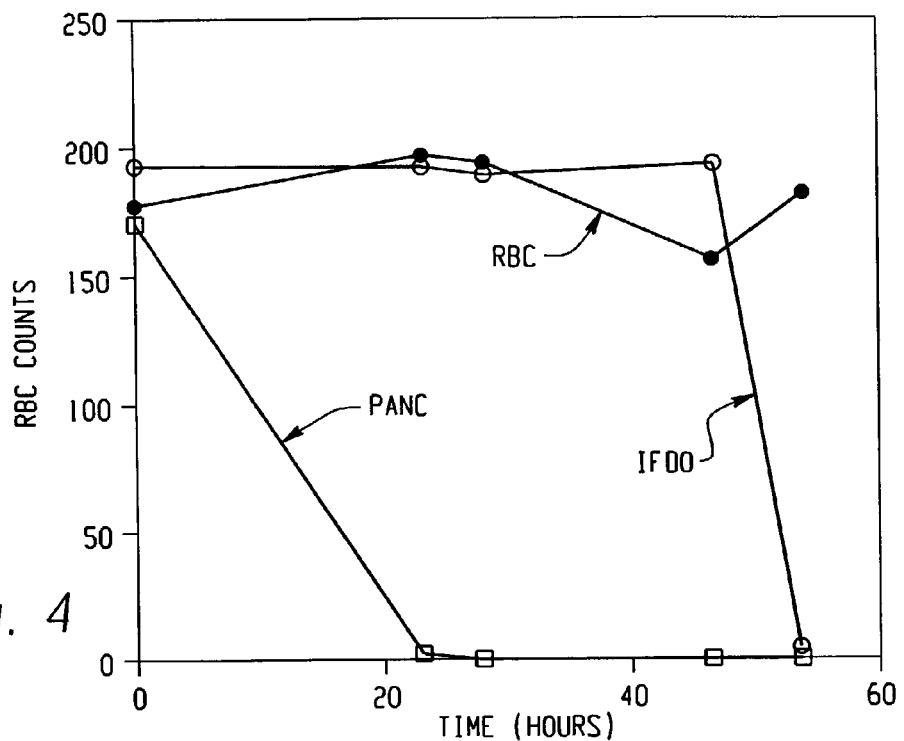
Figure 5:
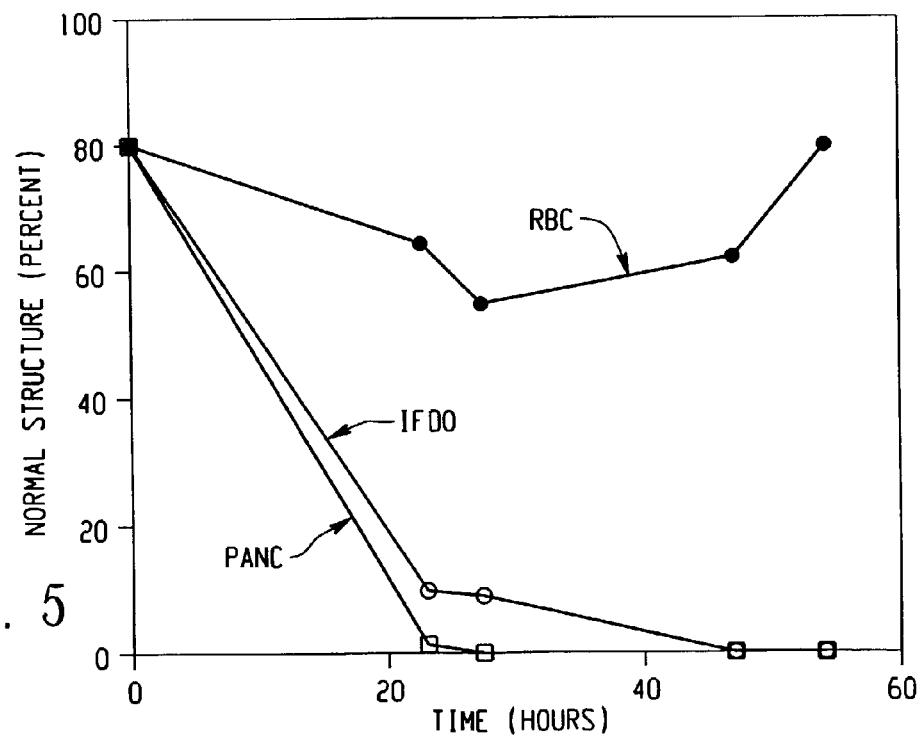

Because of the strong correlations which have been found between the response of prions to various treatments and the corresponding response of the present test protein, the test protein can be used in vitro as a model to screen large numbers of potential drugs, priocidal agents, processes, and the like (all generally referred to as "treatments"), for their potential effect against prions and prion diseases. Treatments which prove to be effective under in vitro studies with the prion model can then proceed to in vivo testing, for example, by inoculating an animal with a prion and subjecting the animal to a treatment regimen (e.g., in the case of a proposed drug for treating a prion disease), or by exposing a prion sample to a selected treatment (such as a proposed priocidal agent for use on medical instruments) and then culturing the exposed sample in vivo, to determine whether the prions have been destroyed by the selected treatment.

Using the prion model, conventional anti-microbial treatments (e.g., peracetic acid, steam, or vapor hydrogen peroxide) can be evaluated for their effectiveness against prions. Modifications to the conventional antimicrobial treatments can be made with a view to optimizing the anti-microbial treatment so that the treatment destroys or otherwise inactivates prions and also destroys or otherwise inactivates other microorganisms typically destroyed by such processes. The modified process can then be used to treat devices contaminated with both prions and with microorganisms. Novel actives, specifically designed for treating prions, can also be evaluated.

Another use for the prion model is to develop treatments for food products, generally those containing an animal product, which may be contaminated with prions. Such products include, for example, raw meat, including meat carcasses, ground meat, or chopped meat products, and cooked meat products, such as sausages, hams, processed meat products and the like. Using the prion model, several treatments have been identified. A method of treating a food product for animal or human consumption which may be contaminated with prions has therefore been developed. The method includes treating the food product with a composition which includes at least one of nisin, manganese, and silver nitrate in a sufficient concentration and for a sufficient time to reduce the level of prions on the food product or to inactivate the prions present. Animal products which are rendered or otherwise prepared for use as animal feedstocks may also be treated with the composition, either before or after rendering.

In another embodiment, a method of treating items, such as medical or dental instruments, which may be contaminated with prions has been developed. The method includes treating the items with a composition which includes at least one of nisin, manganese, and silver nitrate to reduce the level of prions on the items. The concentration of the active in the composition and the length of treatment will depend on the type of active and degree of reduction sought. The treatment may be combined with other treatments known to reduce prions, such as steam autoclaving and/or sodium hydroxide or sodium hypochlorite treatment.

The composition for food or instrument treatment is preferably in liquid form, e.g., an aqueous solution of the active, although dry and non-aqueous compositions are also contemplated. Treatment may include, for example, immersion of the items to be treated in the treatment solution, spraying or otherwise contacting the items with the solution, or exposing the items to a vapor containing the active.

Another treatment method which has been developed using the prion model is to treat items which may have been contaminated with prions with oxidizing agent-based gaseous or liquid processing. As an example, a peracetic acid based solution is used. The method is useful for treatment of medical and dental instruments, and the like, particularly those which have been used for brain or related surgeries. Temperature has been found to have a significant effect on priocidal activity. The peracetic acid solution is preferably at a temperature of from 45–60° C., more preferably, from 53–57° C. It is postulated that a reduction in activity at higher temperatures may be due to coagulation of the protein, rendering it less accessible to the peracetic acid. The temperature range is also effective for destruction of other contaminants, such as microorganisms. This allows the same process to be used for both sterilization and prion reduction or elimination. The peracetic acid solution preferably contains buffers, surfactants, chelants, and may also contain anticorrosives for reducing damage to the instruments or to the treatment system. Surfactants are thought to be particularly important in the formulation, since they may affect the conformational structure of the prion model protein and allow the peracetic acid to be more effective. A peracetic acid concentration of at least 2000 ppm is preferred for rapid prion treatment, more preferably, about 2500 ppm. Peracetic acid concentrations in the range of 2000 to 2500 ppm have been found to break down the protein to a form which is inactive (small peptides or amino acids). Lower temperatures and concentrations are generally less effective. Higher temperatures may be damaging to temperature-sensitive devices and also reduce the half life of peracetic acid.

The peracetic acid treatment can be used to replace conventional, aggressive prion treatments such as steam/NaOH treatments. Or, the peracetic acid treatment can be used in combination with other treatments. One proposed treatment regiment includes:

1. Cleaning the instruments with a cleaning agent which has been found to be effective at removing proteinaceous material, particularly prions;
2. Heat treatment with steam or high temperature (e.g., 180° C.) thermal rinse (optional, or may be carried out after step 3.);
3. Sterilization treatment, e.g., with a peracetic acid formulation at 2000 ppm, or above and a temperature of 55–57° C. for 10–30 minutes.

The cleaning agent is preferably an alkaline cleaning agent or an enzymatic cleaning agent. Tests with the prion model have shown an increase in the effectiveness of the treatment process with the alkalinity of the cleaning product. Highly alkaline products, such as sodium or potassium hydroxide-based products, e.g., CIP™ 100 (obtained from STERIS Corp., Mentor, Ohio) have been found to be particularly effective. Even though termed "highly alkaline," these products have a much lower alkali concentration (CIP™ 100 at 2 oz/gal contains 0.07 M KOH) than the 1N NaOH currently being recommended as a treatment for prions. Thus, a combination of an alkaline cleaning product wash at an alkali concentration of about 0.02M to about 0.1M followed by a peracetic acid treatment is an effective alternative to a treatment with 1N NaOH and is less damaging to the medical instruments or other items being treated.

In another embodiment, a method of screening proposed drugs for activity against prion related diseases or proposed treatment processes or chemicals for priocidal activity has been developed. The method includes exposing a prion model to the proposed drug, chemical, or process and culturing any remaining prion model in vitro. The prion model is one which has been shown to exhibit similar responses to prions to other actives and processes.

In another embodiment, a method for evaluating the effect of a proposed treatment, drug, or other active against prions involves exposing the prion model to the proposed treatment, drug, or other active. After exposure, the prion model (or whatever remains viable) is grown in a suitable growth medium.

For example, in the case of a treatment process, such as a sterilizing process, a coupon or instrument is contaminated with the prion model and exposed to a sterilizing or cleaning treatment. A swab, sample, or extraction is taken after the treatment and is placed in a growth medium. If growth of the prion model is observed, the sterilizing or cleaning treatment has not been fully effective at destruction or removal of prions.

In the case of an evaluation of a potential active, a solution of the drug or other active is mixed with the prion model. After a selected exposure time, an aliquot of the solution is taken and cultured in the growth medium. Prior to culturing, the aliquot is preferably neutralized with a suitable neutralizing agent to inactivate the drug or other active under test. If the drug or active proves effective against the prion model, it can be used in an effective amount to treat a subject, such as a contaminated surface or a person or animal suffering from a prion related disease.

In one embodiment, effects on the growth medium are used as an indicator of residual prion model (and hence, by inference, of prion) activity. The growth medium preferably contains hemoglobin, either in a pure or relatively pure form, or mixed with other blood related products. For example, the growth medium may contain lysed whole blood or lysed red blood cells. If any of the prion model has survived the treatment process or exposure to the selected active, the hemoglobin content of the growth media is reduced as the prion model "grows." This can be observed by a reduction in the deep red color of the media, or by other detection techniques, such as chemical analysis, colorimetry, spectroscopy, or the like. If the media is a solid media, e.g., an agar gel, the color change can be observed as a ring around the prion model, which increases in size over time. Thus, destruction/inactivation of the model may be measured in term of the size of the hemoglobin ring at a particular time after the start of the culturing process. Or, as with liquid media, a change in color of the media may be used as an indication of the amount of prion model remaining.

In one embodiment for testing a proposed treatment process (such as an oxidizing agent-based process, e.g., one using hydrogen peroxide or a peracid alone or in combination, in liquid or vapor form) for destroying prions on medical instruments or other devices, a prion model is contained in a biological indicator of the type conventionally used to test a sterilization or disinfection process for activity against selected, usually relatively hard to kill, microorganisms. One such indicator is exemplified in FIG. 1, although other known biological indicator designs may alternatively be used. The indicator includes a vessel 10, which contains a sample 12 of the prion model, preferably contained within the vessel such that it is not readily washed or otherwise removed from the vessel during the treatment process. The exact mode of containment will depend on the type of treatment process. In the case of liquid sterilants, such as peracetic acid, the prion model is contained within a protein impermeable barrier, which is permeable to the liquid sterilant. For gaseous sterilants, such as vapor hydrogen peroxide, or vapor peracetic acid, the prion model may be simply deposited on an interior surface 14 of a wall of the container or supported on a carrier 16, such as a disk of paper, stainless steel, or polyflex. A suitable growth media may be added to the indicator just before subjecting the indicator to the proposed treatment process. More preferably, the prion model is mixed with a suitable growth media after testing. In one embodiment, a growth media 18 is contained in a penetrable portion or frangible ampule 20 within the vessel and then mixed with the prion model after removal of the indicator form the treatment process. One way to mix the growth medium and the prion model is to break the ampule or penetrate a wall 22 of the portion by movement of a cap 24 from an open position, shown in FIG. 1, in which the sterilant has access to the vessel through openings 26, to a closed position, shown in FIG. 2, in which the cap seals the vessel, preventing exit and entry of fluids. In the embodiment of FIGS. 1 and 2, the cap has a projection 28 which pierces the wall 22. Growth of remaining prion model is observed, for example, by a color change of the media or other detectable change in a physical or chemical property of the media. The color change may be due, for example, to production of the prion model (which appears blackish), reduction in the hemoglobin content of the media, or may be a result of an interaction between the prion model and a chemical indicator present in the media. An observed change in color is indicative that the proposed treatment process would not been effective as a treatment process for prion contaminated devices or other items.

In one embodiment, the indicator contains both a sample of the prion model and a sample of a microorganism which is known to have a high resistance to the type of treatment process under investigation. After subjecting the indicator to the proposed treatment process, the indicator is evaluated for residual prions and/or microorganisms. Treatment processes which are effective against both prions and microorganisms can thus be developed or optimized.

Growth Media

A suitable growth media has been developed for culturing the prion model. The growth media contains an agar or broth base, such as Mycoplasma™ agar or broth base, obtained from Oxoid. A source of hemoglobin, such as washed and lysed red blood cells from a human or other animal, is also present. As discussed above, the red blood cells are preferably tested to make sure that no prions are present in the growth media prior to use. The media also preferably contains a source of proteases. The source of proteases may be an isolated protease, an enzyme extract, which may also contain other enzymes, such as lipases, or a comminuted animal tissue, such as pancreatin, which is obtained by homogenizing pancreas tissue. A dispersing agent, such as Tween 80, is preferably present. Thallium acetate is an optional component for reducing media contamination. The ingredients are blended with water, preferably distilled or other purified water.

The following exemplary growth media has been developed for use with the test protein:

| | |
|---|---|
| Distilled water | 1000 mL |
| agar or broth base (e.g., Oxoid Mycoplasma ™) | 10–100 g |
| Dispersant (e.g., Tween 80) | 0–5 mL |
| Washed and lysed horse red blood cells | 10–40 mL |
| Horse serum | 0–10 mL |
| 0.1 g/mL Pancreatin | 10–40 mL |
| 2% thallium acetate | 2–20 mL |

To test the "viability" of the prion model (e.g., after a proposed treatment process), an aliquot of a culture or dilution containing the prion model is inoculated into a known volume of the above culture media and incubated at around 37° C. for about 48–72 hours. The test proteins will "grow" as a black precipitate in the liquid culture or as discrete 'colonies' under the surface of a culture media plate. Although the prion model is not an organism, as is conventionally understood, the prion model does increase in amount on culturing and hence the term "grow," and similar terms, are used herein to denote an increase in the prion model. The term "viability" is used to denote prion model capable of exhibiting growth, i.e, it has not been destroyed or otherwise inactivated.

To prepare for in vitro tests, liquid cultures of the test protein are rapidly spun down at about 5000×g for about 5 minutes and washed in water or fresh media.

Testing of the simulated priocidal activity can be performed similar to typical tests with bacteria or fungi. These methods include:

1) Minimum inhibitory concentrations (MIC): this method allows for the rapid evaluation of a wide variety of actives to inhibit the culturing of the test protein. In a simple set-up with a microwell plate, serial dilutions of an active are performed and a standard low concentration (e.g., $<10^5$ entity forming units (efu's)) of the prion model in growth media are added to each dilution. Following incubation at 37° C. for 48–72 hours, the presence of growth is indicated by a black precipitate at the base of a well and the lowest concentration of an active to inhibit the growth is recorded as the MIC. This method may be used to identify possible drug targets or biocides for anti-prion activity.
2) Time kill experiments: this method allows for the determination of active or formulation efficacy over time. A test material (e.g., a liquid formulation, product, or active) is prepared at a variety of concentrations and under a variety of environmental conditions (e.g., pH, temperature, presence of a soil, and the like). The prion model culture, at a known concentration, is then directly added to the test liquid and aliquots removed over time for evaluation. The aliquots are preferably neutralized to inhibit further activity of the test material. Evaluation may include serial diluted of the aliquot and plating on selective media to determine the reduction of the test protein over time under the selected test conditions.
   In another test, the culture containing the test protein may be inoculated onto a substrate and exposed to a liquid or gas phase active for selected time exposures. Recoverable test protein is determined by serial dilution and plating.
3) Protein Degradation Studies. Protein containing media (either the test protein or another protein such as one having a high proportion of β sheet structure, similar to prion protein) are subjected to a treatment procedure, such as a peracetic acid treatment, and then aliquots are evaluated by gel electrophoresis or other technique capable of separating out complete proteins from smaller fragments. Several effective priocidal agents have been found to break down the prion protein into smaller fragments. Thus, agents which break down the test protein or other proteins can be viewed as potential prion-treating agents.
   Such tests are valuable for optimizing the effectiveness of a given formulation, active, or process against the test protein. This is particularly important in understanding the effects of formulation and environmental factors on the activity of actives/biocides against prions. Preferably, more than one test is carried out, for example, a time kill study and a protein degradation study are carried out for the proposed treatment before proceeding to evaluate the proposed treatment on prions themselves.

The following examples indicate the effectiveness of the prion model as a model for actual prions and on the effectiveness of various proposed priocidal treatments.

EXAMPLES

Example 1

Growth Media

The following growth media was prepared:

| | |
|---|---|
| Distilled water | 1000 mL |
| Oxoid Mycoplasma ™ agar or broth base | 35.5 g |
| Tween 80 | 2 mL |
| Washed and lysed horse red blood cells | 20 mL |
| Horse serum | 1.4 mL |
| 0.1 g/mL Pancreatin | 20 mL |
| 2% thallium acetate | 7 mL |

When the test protein is inoculated on to a supplemented mycoplasma broth base plated media dish with the formula listed above, and cultured at 37° C., the inoculated spots yield discrete brown colonies on after 48 hours, under aerobic, microaerophilic or anaerobic conditions. No growth is observed at 4° C.

Example 2

Composition of the Test Protein

The test protein was analyzed and determined to contain amino acids, as noted below, and at least two peptides.

When subjected to ICP, primarily iron was observed (although background calcium was seen, presumably all from the media).

Total Amino Acid Analysis

Cultures of the prion model were growth in broth, vigorous washed (by vortexing in saline 5 times) and dried. Samples were submitted for total amino acid analysis. Samples were hydrolyzed for 26 hours in 6N HCl at 110° C., dissolved in 0.01N HCl and analyzed by chromatography.

The results showed the presence of amino acids, with the following percentages:

| | |
|---|---|
| ASP | 8.30% |
| THR | 3.36% |
| SER | 9.08% |
| GLU | 7.38% |
| PRO | 5.24% |

-continued

| | |
|---|---|
| GLY | 10.96% |
| ALA | 7.11% |
| VAL | 5.97% |
| ILE | 2.41% |
| LEU | 12.14% |
| TYR | 1.61% |
| PHE | 3.60% |
| LYS | 5.84% |
| HIS | 11.26% |
| ARG | 5.70% |

Protein Analysis

The prion model protein was solubilized and protein gels were run on the supernatant. SDS-PAGE was used to separate the protein. The presence of a diffuse protein band was observed above the dye front (<10 kDa). This band was transferred onto a membrane by Western blotting and submitted to CCF, Molecular Biology Core for N-terminal sequencing analysis. The signal was weak but indicated two peptide sequences as follows:

K L L/D H/W Q S Q/L H K/M Q R F

I Q K H I L Q K/I M/L A L E

Example 3

Correlation Studies

To demonstrate the effectiveness of time-kill tests, and to establish a correlation between the response of the test protein with that of known prions, the log reduction of test protein was determined using actives known to be effective against prions. Log reduction is the difference between the log of the original number of organisms present (in this case, the number of test proteins, or, alternatively, the concentration of test protein in the sample) and the log of the number remaining. Good correlations were found for such actives. Examples are given below:

a) Peracetic Acid Studies

Specific Peracetic Acid formulations (STERIS 20™ obtained from STERIS Corp., Mentor Ohio) previously proposed as effective priocidal agents were found to be effective against the prion model. STERIS 20™ is a peracetic acid-based sterilant containing buffers, surfactants, chelating agents, and anticorrosives. The results of these tests show that the temperature of the formulation is an important factor. Temperature and active concentration were found to have a surprising and significant effect on both protein and prion inactivation.

i) Protein Degradation Studies

Protein degradation studies were carried out by exposing samples of the prion model to a sterilant (such as peracetic acid) and to control solutions (e.g., water or tris-buffered saline, TBS). After exposure, the peracetic acid was neutralized immediately with sodium thiosulfate (STS) and the sample is separated by gel electrophoresis. Sodium decyl sulfate-polyacrylamide gel electrophoresis (SDS-PAGE) is effective as a protein separating medium. Further, HLC analysis has shown that a major component of the model is a short peptide structure similar to the simple amino acid structure of collagen. The separated proteins were transferred to nitrocellulose by the Western blot method. The presence of particular proteins, such as the prion model, was detected by immunoblotting with monoclonal antibodies specific to the protein and quantified by the percentage intensity of immunostained proteins. Peracetic acid, when used in the particular formulations tested (STERIS 20™), reduced the amount of whole protein, creating smaller peptides, which are regarded as inactivated for purposes of the prion model.

ii) Plating Studies

The efficacy of the peracetic acid formulations under different temperatures and concentrations was studied by suspension testing, using the prion model. Peracetic acid formulations were prepared at 1000, 1500, and 2000 mg/L peracetic acid and maintained at about 50° C. An aliquot of the test protein suspension was directly added to each formulation and samples removed and quantified by serial dilution and plating into modified Mycoplasma agar.

Time kill experiments were carried out to show the effect of time and peracetic acid concentration on the prion model. As an example, the effect of Peracetic acid concentration at 50° C. was shown to be significant (FIG. 3). Following incubation at 37° C. for 48 hours, the plates were counted and log reductions determined. FIG. 3 shows the effect of Peracetic acid concentration (in mg/L) at 50° C. for 12 mins in the STERIS 20™ formulation. At 2000 mg/liter, a log reduction from 9 log (initial concentration) to 2 logs was observed after 6 minutes.

For these tests, the peracetic acid was combined with the buffering system used in the STERIS 20™ formulation, the only differences being in the amount of peracetic acid employed.

These results are similar to a reported reduction of vCJD on Western blots with the same STERIS 20™ peracetic acid formulation (Antloga, et al., *Prion Diseases and Medical Devices, ASAIO J.*, S69–S72 (2000). These results are being confirmed in vivo.

b) Phenolic Formulation Studies

LpH™ is a phenolic formulation sold by STERIS Corporation, Mentor, Ohio. The composition has previously been described as being effective against scrapie in an in vivo study (Ernst & Race, *Comparative Analysis of Scrapie Agent Inactivation Methods, J. Virological Methods*, 41, pp. 193–202 (1993)). The authors described the loss of scrapie infectivity dependent on the concentration and time of exposure. For example, at a concentration of 0.9%, the infectivity removed, as measured by log reduction, was 5 logs after 0.5 hours and over 7 logs at 16 hours. Similarly, at 9%, an over 7 log reduction was observed at 0.5 hours.

The activity of the LpH™ product was tested on samples of the test protein at a 5% LpH™ concentration. The results indicated a 5.2 log reduction at 1 hour and a 5.8 log reduction at 3 hours. Further, the product was shown to be more effective than a similar product LpHse™. The same differences between LpH™ and LpHse™ which has also been shown by Race for prions (unpublished results).

Example 4

Optimization of Peracetic Acid Treatment of Prion Model Samples

Testing using protein degradation as a screening tool has shown that a peracetic acid concentration of about 2000 mg/L or above is preferred for efficacy against the test protein (FIG. 3). These tests were carried out using STERIS 20™.

The effect of temperature on the test protein formulation (studied at 1000 mg/L peracetic acid) was found to be dramatic. The results preliminarily indicate that the peracetic acid formulation is highly effective at breaking down protein within the range of 50–57° C. at the times tested in this study. Little to no breakdown was observed at temperatures below 50° C. At about 60° C., or above, similar loss in activity was observed. A temperature of about 55–57° C. has been found particularly effective.

Example 5

MIC Investigations

The effects of a variety of actives (many with previous reports of possible effects on prions) in MIC (growth inhibition) tests on the prion model were studied.

The following actives showed at least some effect on growth characteristics of the prion model (i.e., a reduction in the growth of the prion model):
nisin (1000 mg/L)
Klenzyme™ (5%) (obtained from STERIS Corp.)
Renuklenz™ (5%) (obtained from STERIS Corp.)
NaOH (0.01N)
HCl (0.1N)
Peracetic acid (600 mg/L)
neomycin sulphate (125 mg/L),
LpH™ (Obtained from STERIS Corp, Mentor, Ohio) (1–5%)
LpHse™ (Obtained from STERIS Corp, Mentor, Ohio) (1–5%)
Manganese (100 mg/L)
silver nitrate (30 mg/L)

Example 6

Removal Tests

A variety of cleaning agents were evaluated. Instruments were contaminated with Bovine Serum Albumin (BSA-a protein). To make the protein more difficult to remove, the instruments were heated at 110° C. for one hour to denature the protein. The instruments were then washed in an automated washer using 1 oz./gal. of a cleaning agent and a high wash temperature (150° C.). After the washing cycle, visual examination for remaining soil was carried out. The cleaning agents evaluated are listed below in order of decreasing effectiveness. All the cleaning products were obtained from STERIS Corp., Mentor, Ohio.

CIP 100™ (a sodium hydroxide-based cleaner)—Most effective
CIP 150™ (a potassium hydroxide-based cleaner)
Process Klenz™
Criti-Klenz™
Renu-Klenz™ (a neutral product)
CIP 220™ (an acid-based cleaner)
Water—least effective The above order of effectivity also generally follows (with the exception of water) the alkalinity of the product. The most effective cleaning product, CIP 100™, also has the highest alkalinity. The least effective, CIP 220™, is acidic.

The same order of effectivity was found when the prion model was used in place of BSA.

Example 7

Red Blood Cells Viability Assay

The prion model was found to adsorb/use hemoglobin or Red blood cells (RBCs) components in the growth media. A study of the effect of the prion model on whole red blood cells was carried out. RBCs were washed in saline 3 times and resuspended at a concentration to count cells under a Petroff Hauser at 40× (100/field). Total red blood cells and the percentage of cells which were still intact (unchanged in morphology) were monitored over time following incubation with the prion model (IFDO) or with water (RBC) or pancreatin (Panc-this had been shown in preliminary experiments to lyse RBCs).

The results, shown in FIGS. 4 and 5, indicate that the prion model caused cell damage and lysis over time, when compared to the controls(RBC and Panc). There appears to be a lag time before red blood cells are lysed by the prion model.

Example 8

Time Kill Experiments

Preliminary time kill experiments were conducted with the prion model. Results are expressed as log numbers ($log_{10}$), the lower the log number, the fewer the prions remaining and thus the more effective the treatment.

Time kill experiments were carried out to show the effect of autoclaving the prion model at 121° C. in saline solution. The prion count dropped from 8.0 logs initially to 5.5 logs after 15 minutes.

Preliminary studies in a gravity drain cycle for 1 hour at 134° C. showed the treatment was effective.

Time kill experiments were carried out to show the effect of ethylene oxide on coupons treated with the prion model. Coupons exposed at 600 mg/L for 18 mins.

| | Prion count in Logs |
|---|---|
| Initial count | 8.5 |
| Exposure at 70° C., 100% RH | 5.0 |
| Exposure at 54° C., 40% RH | 4.7 |

As with peracetic acid, similar temperature effects were found, the ethylene oxide being more effective at 54 than at 70° C.

Liquid Disinfectants/Sterilants were evaluated in time kill studies for their effectiveness against the prion model. All of the products were obtained from STERIS Corp. Samples of the prion model in liquid suspension were directly inoculated into each product. The results are shown below.

| Treatment | Time of Exposure (hrs) | Log No. of Prion Model |
|---|---|---|
| Initial count | 0 | ~6.6 |
| 10% CIP220 ™ | 1 | >3.0 |
| 10% CIP220 ™ | 3 | >3.0 |
| LpH ™ | 1 | 1.4 |
| LpH ™ | 3 | 0.8 |

Example 9

Investigation of Intrinsic Contamination

Blood products were screened for contamination with prions. The following levels of contamination were found:

Horse blood (1 lot) contaminated
Horse serum (1 lot) contaminated

Bovine serum (3 lots) one lot contaminated Sheep's blood (2 lots) none contaminated The results indicate that prion contamination of blood products is common and therefore all blood products to be used in prion-related work should be screened for prions prior to use.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method for evaluation of candidate treatments for in vitro activity against prions on surfaces known or suspected of being contaminated with prions which cause prion-related diseases, comprising:

subjecting a prion model comprising an ileal fluid dependent organism (IFDO) to a candidate treatment which includes contacting the prion model in vitro with a peracid, the prion model being one which has been shown to exhibit a response similar to that of prions to a treatment that attacks prions; and evaluating the effect of the candidate treatment on the prion model as an indicator of the effect of the candidate treatment on the surfaces known or suspected of being contaminated with prions.

2. A method for evaluation in vitro of candidate treatments for activity against prions on surfaces known or suspected of being contaminated with prions which cause prion-related diseases, comprising:

subjecting an ileal fluid dependent organism (IFDO) prion model to a candidate treatment, the prion model exhibiting a response similar to that of prions to a treatment that attacks prions;

culturing any remaining prion model in a medium containing hemoglobin, and observing a change in color of the medium as an indication of the amount of prion model remaining; and evaluating the effect of the candidate treatment on the IFDO prion model as an indicator of the effect of the candidate treatment on the surfaces known or suspected of being contaminated with the disease-causing prions.

3. A method for in vitro evaluation of potential treatments for activity against prions in vitro on surfaces known or suspected of being contaminated with prions which cause priori-related diseases, comprising:

subjecting a prion model comprising an ileal fluid dependent organism (IFDO) to a potential treatment which includes treating the prion model with a peracetic acid solution at a temperature of 50–58° C., the prion model being one which has been shown to exhibit a response similar to that of prions to a treatment designed to attack the prions which cause prion-related diseases; and evaluating the effect of the treatment on the prion model as an indicator of the effect of the treatment on the surfaces known or suspected of being contaminated with prions different from the prion model.

4. The method of claim 1, wherein the prion model is contained in a vessel which includes a path by which the candidate treatment contacts the prion model, the path providing a challenge to the access of the candidate treatment which is at least as challenging as that posed by a device containing a prion contaminated surface to be treated by the candidate treatment in a successful candidate treatment.

5. The method of claim 2, wherein the candidate treatment includes a candidate treatment process which is known to be effective at destroying microorganisms.

6. The method of claim 5, wherein the candidate treatment process includes contacting the prion model with at least one of the group consisting of hydrogen peroxide and peracids.

7. A method of evaluating an in vitro candidate treatment of surfaces of a medical or pharmaceutical device known or suspected of being contaminated with prions, comprising:

subjecting a prion model in vitro to the candidate surface treatment, the prion model being one which exhibits a response similar to that of prions to other treatments designed to attack prions; the candidate treatment including:

treating a surface of a medical or pharmaceutical device which has been contaminated with the prion model with a candidate composition which includes at least one of nisin, manganese, and silver nitrate; and evaluating the effect of the candidate treatment on the prion model as an indicator of the effectiveness of the candidate treatment on the surfaces of medical or pharmaceutical devices contaminated with prions.

8. A method for evaluating candidate treatments for activity against prions comprising:

applying a prion model to a substrate, the prion model comprising an ileal fluid dependent organism (IFDO) which has been shown to exhibit a response similar to that of the prions to another treatment designed to attack prions;

subjecting the prion model to a candidate treatment, the potential treatment including:

cleaning the substrate with a cleaning composition which removes proteins; and contacting the cleaned substrate with a candidate oxidizing agent; and evaluating in vitro the effect of the candidate treatment on the prion model as an indicator of the effect of the candidate treatment on the prion.

9. The method of claim 1, wherein the step of evaluating includes:

culturing remaining prion model in a growth medium; and detecting growth of prion model.

10. The method of claim 9, wherein the step of detecting includes subjecting the cultured prion model to a procedure which detects proteins.

11. A method of screening chemicals or processes for in vitro priocidal activity comprising:

exposing a prion model comprising an ileal fluid dependent organism in vitro to the proposed chemical or process, the prion model having been shown to exhibit similar responses to prions to other chemicals or processes;

culturing any remaining prion model in vitro, including growing the remaining prion model in a media containing hemoglobin, and observing a change in color of the media as an indication of the amount of prion model remaining.

12. The method of claim 11, further including:

subjecting the cultured prion model to a procedure which detects proteins.

13. The method of claim 12, wherein the procedure detects protein fragments.

14. The method of claim 1, wherein the surface is a surface of biological tissue.

* * * * *